United States Patent [19]

Albert

[11] 4,315,744
[45] Feb. 16, 1982

[54] CHUCK WRENCH FOR DENTAL HANDPIECES

[76] Inventor: Thomas W. Albert, 131 E. McClelland, Bartlett, Ill. 60103

[21] Appl. No.: 109,395

[22] Filed: Jan. 3, 1980

[51] Int. Cl.³ .............................................. A61C 7/08
[52] U.S. Cl. .................................. 433/126; 279/1 K; 81/90 A
[58] Field of Search ............... 433/129, 126; 81/90 A; 279/1 K

[56] References Cited

U.S. PATENT DOCUMENTS 3,325,899 6/1967 Staunt ................................... 433/129
3,465,442 9/1969 Baldwin et al. ...................... 433/129
3,888,008 10/1975 Lake et al. ........................... 433/129
3,935,761 2/1976 Junkel ..................................... 81/55

Primary Examiner—Robert Peshock

[57] ABSTRACT

A chuck wrench for dental handpieces in which the wrench has a unitary handle that may be easily gripped by a user for coupling the wrench to the head of a handpiece for adjusting the collet chuck thereof. The wrench includes a rigid shaft of non-circular cross section secured to the wrench body and at least one spring-loaded lug pin located alongside the shaft for keying the rotor of the handpiece to the handpiece cap.

19 Claims, 5 Drawing Figures

CHUCK WRENCH FOR DENTAL HANDPIECES

BACKGROUND

Staunt U.S. Pat. No. 3,325,899 discloses a wrench having a two-piece body, one section 32 of the body having a central shaft 31 of non-circular cross section secured thereto and the other section 33 being provided with a plurality of fixed pins 40 for locking the rotor and cap of a handpiece together when the wrench is in use. Once the lower section 33, pins 40, cap D, and rotor (particularly burtube 15) are keyed together, the upper section 32 of the wrench may be turned one way or the other to adjust the collet chuck of the handpiece.

Such wrench is still in widespread use, its popularity being attributable at least in part to the relatively compact design which permits it to be gripped between the fingers for one-handed wrench operation. While such wrench has significant advantages over prior constructions and is not difficult to manipulate properly, it nevertheless requires the exercise of some skill for correct wrench operation. Normally, the user grips the wrench by holding upper section 32 between the fingers of one hand and then guides shaft 31 into the head of the handpiece through the central opening in cap D. When pins 40 engage the cap's top surface, the user proceeds to turn the wrench in his fingers until the pins enter the outer openings in the cap. If, in an effort to hasten the entry of such pins into such openings, the user exerts an axial force on the wrench, the increased frictional resistance between the tips of pins 40 and the cap's top surface tends to resist sliding movement of the parts and may have a negative effect in hastening entry of the pins.

After the pins have been inserted into the outer openings of the cap, the user simply rotates the upper section 32 until the handpiece rotor assembly has been turned sufficiently to bring the apertures of the rotor into alignment with the cap openings and pins. The pins 40 may then enter the apertures 43 of the rotor and lock the rotor, cap, and lower wrench section 33 against relative rotation. Thereafter, rotation of the upper section 32 causes tightening or loosening of the chuck.

Ordinarily, the force required in such a tightening or loosening operation may be applied with little effort; however, if the chuck of the handpiece has been over-tightened in a previous operation, a proportionately greater rotational force must be applied to the upper section 32 to turn the chuck and release the dental bur. Should such greater rotational force be applied to both sections 32 and 33 of the wrench, rather than just to upper section 32, the user may find that he has inadvertently unthreaded cap D from the head C of the handpiece instead of effecting a release of bur E.

Inexperienced or careless wrench operation may result in other problems as well. FIG. 4 of U.S. Pat. No. 3,325,899 shows a small but definite spacing between the underside of wrench F and the top surface of cap D. Such spacing, to a greater or lesser extend, is necessary in order to insure bottoming of pins 42 in rotor apertures 43. However, such spacing also gives rise to the possibility that should the wrench be misused, especially in a way that involves the application of excessive force in either a tightening or loosening operation, the wrench might be canted out of axial alignment with the handpiece, causing a bending of pins 40 or shaft 31 of the wrench and possible serious damage to the handpiece itself.

The possibilities of misalignment may be reduced somewhat by wrenches of later design, such as those disclosed in Lake-Jaremus U.S. Pat. No. 3,888,008 and Junkel-Kneipper U.S. Pat. No. 3,935,761, but at the expense of increased bulk and at least apparent increased complexity. The wrenches of both of these patents are directed to systems in which the wrench operates to hold the chuck (rather than the rotor) stationary while the rotor (not the chuck) is turned. While it is possible to hold and operate the wrench of U.S. Pat. No. 3,935,761 in one hand, dentists commonly regard such wrench as one requiring two-handed operation—one hand for the purpose of holding the wrench and maintaining the head of the handpiece within shroud 15, and the other for rotating wheel 27. Neither of these patents, unlike U.S. Pat. No. 3,325,899, involves a wrench which utilizes the relatively simple but highly effective concept of securing a rotor against rotation by keying it to the cap of the handpiece through the use of pins which extend through the cap and into the rotor.

Other patents concerned with handpiece wrenches and disclosing the state of the art are U.S. Pat. Nos. 3,947,966, 3,960,039, 4,015,335, 4,020,556, and 3,499,223.

SUMMARY OF INVENTION

A main aspect of this invention lies in providing a compact wrench which is easily operated and which does not allow for misuse by the user. Such wrench may be easily gripped and operated by the fingers of one hand. Although it utilizes an operating principle of U.S. Pat. No. 3,325,899 (that of keying and immobilizing the rotor with respect to the handpiece cap), it cannot be operated inadvertently to loosen the cap and is virtually impossible to manipulate in a manner that would cause damage to the wrench and particularly to the delicate parts of the handpiece.

In brief, the wrench comprises a unitary elongated wrench body having a longitudinal axis of rotation and terminating at one end in an end surface lying along a plane normal to that axis, a rigid shaft of non-circular cross sectional configuration secured to the body and extending from the end surface along the wrench's longitudinal axis, and at least one lug pin disposed in spaced parallel relation with the shaft, such lug pin being supported by the wrench body for limited longitudinal movement between retracted and extended positions. In the best mode presently known for practicing the invention, a plurality of such lug pins are provided, such pins all being mounted upon a support ring disposed within an end cavity of chamber of the wrench body. A spring within the chamber urges the ring axially outwardly to extend the lug pins, and an annular stop engages the ring to limit the extent of outward travel of such pins.

In operation of the wrench, the user simply inserts the non-circular central shaft through the center opening in the end cap of the handpiece and into the non-circular opening of the chuck disposed within that handpiece. The shaft pilots longitudinal movement of the wrench, guiding such movement until the ends of the spring-loaded pins are in direct surface engagement with the face of the handpiece's end cap. The user then simply rotates the wrench body, maintaining the ends of the retracted or partially-retracted pins in contact with the end cap, until the spring-loaded pins sweep into alignment with the outer openings in the cap and enter such openings. Continued rotation of the wrench body may then proceed independently of the pins, since the latter are received within the lateral openings of the end cap, and such rotation causes the chuck and rotor of the handpiece to turn until the recesses of the rotor align with the outer end cap openings and permit the pins to enter such recesses. As the spring-loaded pins advance into the recesses of the rotor (burtube) and bottom in such recesses, a sharp click signals that the pins are fully in place and key the rotor and the cap of the handpiece together. Further rotation of the wrench body, now with the end face of that body in surface engagement with the cap of the handpiece, causes the collet chuck to turn (because of force transmitted through the non-circular shaft) independently of the rotor (which is locked to the handpiece cap by the lug pins).

The length of the lug pins is such that when the wrench is disengaged from the handpiece the extension of the pins from the body under the influence of the springs is greater than when the wrench is fully coupled to a handpiece. As a result, the pins necessarily extend the full depth of the rotor recesses when the wrench is in its operative position. This insures full locking engagement between the lug pins and rotor while at the same time eliminating any spacing between the end surface of the wrench and the handpiece's end cap, and also causes the emanation of the audible signal as the lug pins engage the bottom surfaces of the rotor recesses.

Other features, advantages, and objects of the invention will become apparent from the drawings and specification.

DRAWINGS

DETAILED DESCRIPTION OF PREFERRED EMBODIMENT

Figure 1:
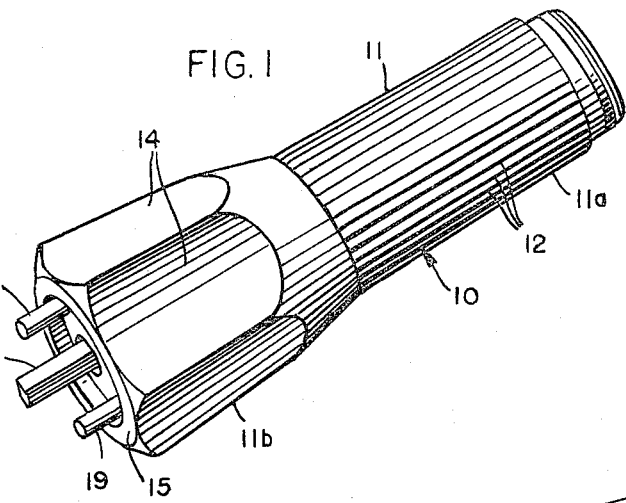
FIG. 1 is a perspective view of a handpiece chuck wrench embodying the invention.

Referring to the drawings, the numeral 10 generally designates a wrench having an elongated wrench body 11. The body has a cylindrical rear portion 11a and an enlarged reversely-tapered front portion 11b. The body is of unitary one-piece construction and, consequently, the two portions 11a and 11b are integrally formed. The rear portion is provided with longitudinal ribs 12 to facilitate rotation of the handle between the fingers about a longitudinal rotational axis indicated at 13 in FIG. 2. The flared configuration of the front portion 11b helps to keep a user's fingers from sliding forwardly beyond rear portion 11a when the wrench is in use, and the flat surfaces 14 about the front portion prevent the wrench from rolling upon a table or other support surface.

Figure 2:
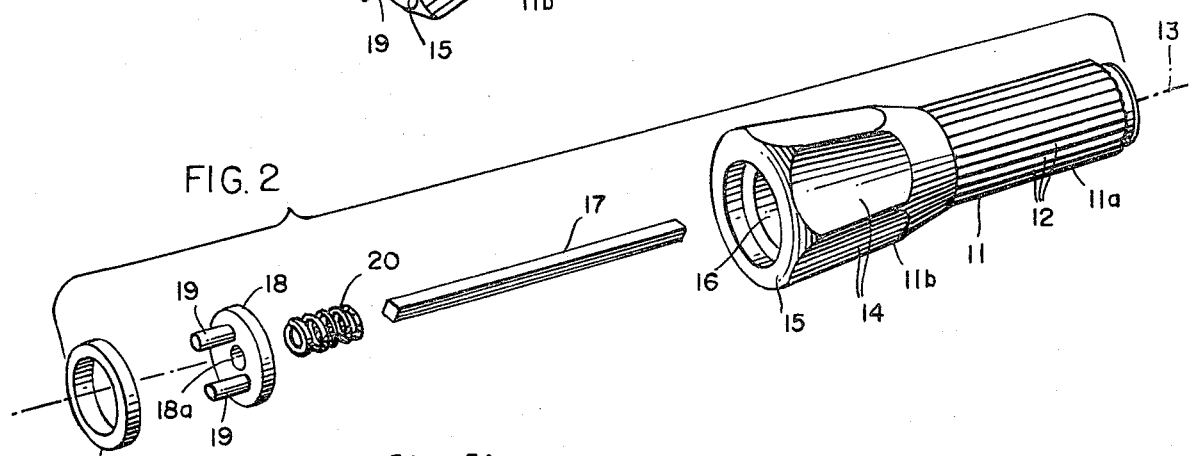
FIG. 2 is an exploded perspective view of the wrench.
Figure 3:
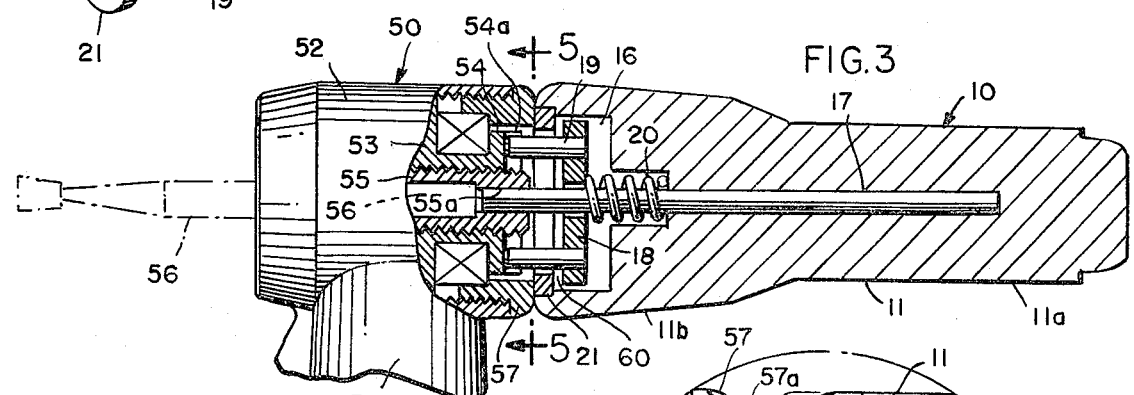
FIG. 3 is a sectional longitudinal view of the wrench showing it in full operative engagement with a dental handpiece.

The wrench has an annular front surface or face 15 which extends along a plane normal to the longitudinal axis 13 of the handle or body 11. A cavity 16 extends inwardly from the front face and, as shown in FIGS. 2 and 3, is of stepped cylindrical configuration. A straight rigid shaft 17 of non-circular cross sectional configuration is fixed to the body and projects forwardly therefrom through cavity 16 and beyond end face 15. While the non-circular shaft 17 is shown to be of square cross section, it is to be understood that it may be hexagonal or whatever other cross sectional configuration is required for permitting it to mate with the chuck of a handpiece with which the wrench is intended to be used.

Within cavity or chamber 16 is a support ring 18 which carries a pair of lug pins 19. Only a single pin is necessary for an operative assembly; however, a plurality of such pins is preferred in order to achieve a secure interlock with the rotor (burtube) of a handpiece when the wrench is in use. The central aperture 18a of the ring loosely receives shaft 17 to permit rotation of the ring independently of the shaft. A helical compression spring 20 also extends about the shaft behind the ring and urges the ring forwardly towards the open end of the cavity. A stop member in the form of a ring 21 having a smaller inside diameter than the outside diameter of support ring 18 is secured by welding or by any other suitable means to the mouth of the cavity to limit the extent of forward movement of the support ring under the influence of spring 20.

Both the length of the pins 19 and the depth of cavity 16 are important. The cavity should be deep enough to permit substantial retraction of the pins whereas the pins must be long enough to project a distance greater than that required to reach the ends of the rotor recesses when such pins are fully extended, that is, when spring 20 has urged the front face of ring 18 into contact with stop member 21.

The relationships are best understood by considering the wrench in operative engagement with a handpiece. FIG. 3 depicts a turbine-driven contra angle handpiece 50 having a handle 51 terminating in a head housing 52. Within the housing is a rotor assembly 53 which includes what is commonly referred to as a burtube portion 54. The burtube is internally threaded to receive a collet chuck 55. The chuck may be similar in construction to the chuck disclosed in the aforementioned U.S. Pat. No. 3,325,899, having spring jaws for gripping a dental bur 56. Rotation of the chuck 55 in one direction relative to the burtube 54 causes a tightening of the jaws about the shank of the bur, whereas relative rotation in the opposite direction produces a loosening of such jaws.

Figure 5:
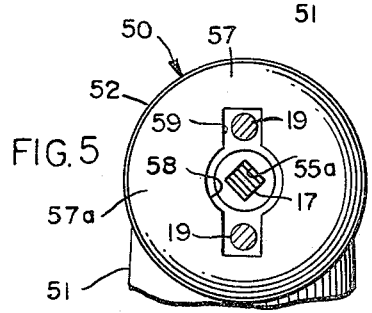
FIG. 5 is an end view of the handpiece taken along line 5—5 of FIG. 3.
Figure 4:
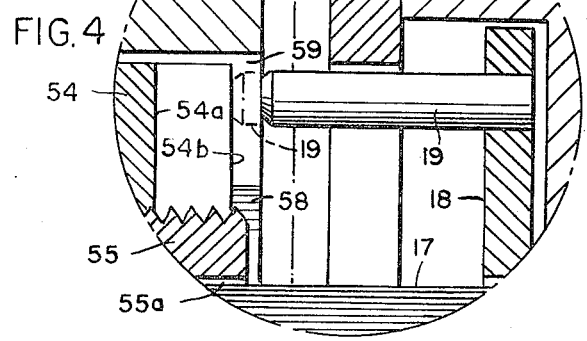
FIG. 4 is an enlarged view of certain elements depicted in FIG. 3 but showing the relationship of parts just before the lug pins have entered the openings of the cap and the recesses of the rotor.

The end of the head housing opposite from bur 56 is closed by an end cap 57 which is threadedly connected to the housing and which has a planar outer end surface 57a lying along a plane normal to the rotational axis of the rotor. A central opening 58 in the end cap exposes the end of the chuck 55 and, in particular, reveals the non-circular opening 55a at the end of that chuck. As shown in FIG. 5, the chuck opening may be square in cross sectional configuration; however, other non-circular configurations, such as a hexagonal cross sectional configuration, may be provided. What is important is that the opening 55a be dimensioned to receive the projecting end of non-circular wrench shaft 17 to lock the wrench body 11 and chuck 55 against independent relative rotation when the parts are assembled as shown in FIGS. 3–5.

End cap 57 also includes at least one lateral opening 59. Preferably more than one of such openings is provided. In the embodiment shown, two such openings are disposed at diametrically opposite sides of central opening 58 and are depicted as lateral extensions of that central opening. When the wrench is fully coupled to the handpiece, pins 19 of that wrench extend through lateral openings 59 and are received within diametrically-disposed recesses 54a at the end of burtube 54. Such relationship is shown in FIG. 3.

It is to be noted from FIG. 3 that the annular end face 15 of the wrench body is in direct surface engagement with the planar end face 57a of end cap 57. Under such conditions, with pins 19 extending through cap openings 59 and into burtube recesses 54a, so that the ends of the pins extend the full depth of such recesses and are bottomed therein, there remains a slight but definite spacing 60 between support ring 18 and stop member 21. In other words, pins 19 have not quite reached their fully extended positions under the force of spring 20 even when such pins have bottomed within recesses 54a. Such a relationship provides ample reserve to insure that the locking pins will extend the full depth of the recesses 54a of a handpiece regardless of dimensional variations within the range of manufacturing tolerances. Since the pins are always capable of bottoming within the recesses, the optimum degree of interconnection between the parts is assured regardless of such dimensional variations. Also, since such bottoming involves forceful contact between the ends of the pins and the end walls of the recesses, an audible signal is produced when complete interconnection has been effected.

The spring loading of the pins also allows surface engagement between the end face 15 of the wrench and the outer surface 57a of the cap when the parts are fully coupled and, because of such surface engagement, the possibilities of the wrench being canted out of axial alignment with the handpiece are eliminated or at least greatly reduced.

In use, the wrench is simply held between the fingers of one hand and is guided so that the protruding end of non-circular shaft 17 (which extends a substantial distance beyond the ends of extended pins 19, as shown in FIG. 1) enters the central opening 58 of end cap 57 and is received within the non-circular opening 55a of chuck 55. As the parts are urged together, the spring-loaded pins ordinarily first engage the outer surface of the end cap 57, resulting in partial pin retraction as the spring is compressed (FIG. 4). Limited rotation of the wrench then causes the retracted pins to slide over the cap's end surface until they reach the lateral openings 59 and, under the force of spring 20, are driven into such openings. In this regard, it is to be noted that spring 20 performs a clutching function in coupling ring 18 and wrench body 11 for simultaneous rotation notwithstanding the resistance to rotation of the ring imposed by frictional engagement between pins 19 and the end surface of cap 57. Stated differently, the resistance imposed by the spring to independent rotation of ring 18 and pins 19 is greater than the frictional resistance generated by the pins traveling in their arcuate paths in contact with the end cap.

As soon as the pins enter the lateral openings 59 in the end cap the parts typically assume the relationship represented by broken lines in FIG. 4. Continued rotation of the wrench causes further rotation of the chuck 55 and burtube 54 but, since the pins 19 are now received within the lateral openings of the end cap, further rotational movement of the pins and support ring 18 is prevented. Therefore, as the chuck is turned about its rotational axis 13, the end surface 54b of the burtube sweeps about the ends of the pins until burtube recesses 54a move into alignment with the pins. At that moment, spring 20 drives the pins into recesses 54a to key the burtube, and the rotor of which it is a part, to the end cap 57 of the handpiece. The rotor is therefore locked against further rotation and, as the user continues to turn the wrench, now with the end face 15 of the wrench in direct surface engagement with cap 57, chuck 55 is turned one way or the other with respect to the rotor to tighten or loosen the gripping force of that chuck upon bur 56.

While in the foregoing an embodiment of the invention has been disclosed in considerable detail for purposes of illustration, it will be understood by those skilled in the art that many of these details may be varied without departing from the spirit and scope of the invention.

I claim:

1. A chuck wrench for dental handpieces comprising an elongated wrench body having a longitudinal axis of rotation and being dimensioned to be gripped between a user's fingers for one-handed rotation; a rigid shaft of non-circular cross section secured to said body and extending from one end thereof along said axis of rotation; at least one lug pin disposed alongside said shaft in spaced parallel relation therewith; means supporting said pin with respect to said body for rotational movement between retracted and extended positions; stop means provided by said body for limiting movement of said pin in said extended position; and spring means urging said pin into said extended position and frictionally engaging both said pin-supporting means and said body to provide limited frictional clutching resistance to independent relative rotation of said pin-supporting means and said body about said axis; said shaft extending a substantial distance beyond said pin when said pin is in its extended position.

2. The wrench of claim 1 in which a plurality of said lug pins are provided; said pins being equidistant from said axis of rotation.

3. The wrench of claim 2 in which said support means comprises a ring extending about said shaft and interposed between said pins and said spring means.

4. The wrench of claim 3 in which said spring means comprises a helical compressional spring extending about said shaft between said ring and said body.

5. The wrench of claim 1 in which said one end of said body terminates in an end face extending along a plane normal to said axis of rotation.

6. A chuck wrench for dental handpieces comprising an elongated wrench body having a longitudinal axis and terminating at one end in an end face lying along a plane normal to said axis; said body having a cavity extending inwardly from said end face; a rigid shaft of non-circular cross section secured to said body and extending beyond said end face along said longitudinal axis; at least one lug pin disposed in spaced parallel relation with respect to said shaft; support means within said cavity supporting said lug pin for rotational movement circumscribing said longitudinal axis and for limited longitudinal movement between a retracted position and an extended position wherein said pin projects from said body beyond said end face; stop means for limiting movement of said pin in said extended position; and spring means urging said pin into said extended position and frictionally engaging both said pin-supporting means and said body to provide limited frictional clutching resistance to independent relative rotation of said pin-supporting means and said body about said axis.

7. The wrench of claim 6 in which said shaft extends substantially beyond said pin when said pin is in its extended position.

8. The wrench of claim 6 in which a plurality of said lug pins are provided; said pins being disposed equidistant from said longitudinal axis.

9. The wrench of claim 8 in which a pair of said pins is provided; said pins being diametrically disposed on opposite sides of said shaft.

10. The wrench of claim 8 in which said support means comprises a ring extending about said shaft and interposed between said pins and said spring means; said pins being rigidly secured to said ring.

11. The wrench of claim 10 in which said spring means comprises a helical compression spring extending about said shaft and disposed between said ring and said body.

12. A chuck wrench for dental handpieces comprising an elongated wrench body having a longitudinal axis and terminating at one end in an end face lying along a plane normal to said axis; a cavity extending axially into said body from said end face; a straight rigid shaft of non-circular cross section secured to said body and extending through said cavity and projecting beyond said end face along said longitudinal axis; a support ring rotatably disposed within said cavity for rotation about said longitudinal axis and provided with at least one lug pin extending alongside said shaft in spaced parallel relation therewith; said ring and pin being movable axially between retracted and extended positions; stop means fixed to said body for engaging said ring and limiting movement of the same in said extended position; and spring means within said cavity urging said ring and pin into said extended position, said spring means frictionally engaged both said ring and said body to provide limited frictional clutching resistance to independent relative rotation of said ring and body about said longitudinal axis.

13. The wrench of claim 12 in which said shaft extends substantially beyond said pin when said pin is in its extended position.

14. The wrench of claim 12 in which a plurality of said lug pins are provided; said pins being spaced equidistant from said longitudinal axis.

15. The wrench of claims 12, 13, or 14 in which said spring means comprises a helical compression spring extending about said shaft within said cavity and engaging said ring to urge the same into said extended position.

16. In combination with a dental handpiece having a handle terminating in a head housing having a cap at one end thereof, a rotor disposed within said housing and having an axial bore therethrough, and a tubular chuck threadedly mounted within said bore, said chuck having a non-circular axial opening and communicating with a central aperture in said cap, and said rotor having at least one recess alongside said opening and alignable with a lateral aperture in said cap, wherein the invention is characterized by a chuck wrench comprising an elongated wrench body having a longitudinal axis of rotation adapted to be aligned with the rotational axis of said rotor and having an end face adapted to be positioned in surface contact with said cap, a rigid shaft of non-circular cross section secured to said body and extending from said end face along said longitudinal axis, said shaft being dimensioned to be received within said noncircular axial opening of said chuck through said central aperture of said cap, at least one lug pin disposed in spaced parallel relation with respect to said shaft, support means supporting said pin for rotational movement circumscribing said axis and for limited longitudinal movement between a retracted position and an extended position wherein said pin projects axially from said body through said lateral aperture of said cap and into said recess of said rotor, stop means for limiting the extent of movement of said pin in said extended position, and spring means urging said pin into said extended position and frictionally engaging both said pin-supporting means and said body to provide limited frictional clutching resistance to independent relative rotation of said pin-supporting means and said body about said axis; said shaft extending a substantial distance beyond said pin when said pin is in its extended position.

17. The combination of claim 16 in which said pin is dimensioned to exceed the length required to extend the full depth of said recess when said pin is in its extended position and the end face of said wrench is in surface contact with said cap.

18. The combination of claim 17 in which said body is provided with a cavity extending inwardly from said end face, said support means comprising a ring extending about said shaft and disposed within said cavity, said pin being rigidly secured to said ring, said stop means being fixed to said body and being engagable with said ring to limit the maximum extension of said pin, said ring being spaced axially from said stop means when said pin is fully received within said recess and said end face of said wrench is in surface engagement with said cap.

19. The combination of claims 16, 17, or 18 in which a plurality of said pins are provided, said pins being spaced equidistant from said shaft.

* * * * *

UNITED STATES PATENT AND TRADEMARK OFFICE
CERTIFICATE OF CORRECTION

PATENT NO. : 4,315,744
DATED : February 16, 1982
INVENTOR(S) : Thomas W. Albert

It is certified that error appears in the above-identified patent and that said Letters Patent are hereby corrected as shown below:

On the cover page, after the name and address of the inventor, insert:

[73] Assignee: American Hospital Supply Corporation, Evanston, Ill.

Signed and Sealed this

Eighth Day of June 1982

|SEAL|

Attest:

Attesting Officer

GERALD J. MOSSINGHOFF

Commissioner of Patents and Trademarks